(12) United States Patent
Nishio

(10) Patent No.: US 7,558,624 B2
(45) Date of Patent: Jul. 7, 2009

(54) APPARATUS FOR REVERSE IONTOPHORESIS AND METHOD FOR REVERSE IONTOPHORESIS

(75) Inventor: Mitsuhiro Nishio, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1260 days.

(21) Appl. No.: 10/691,825

(22) Filed: Oct. 23, 2003

(65) Prior Publication Data

US 2004/0188256 A1    Sep. 30, 2004

(30) Foreign Application Priority Data

Oct. 23, 2002    (JP)    ............................ P2002-308574

(51) Int. Cl.
*A61N 1/30*    (2006.01)
(52) U.S. Cl. ........................................................ 604/20
(58) Field of Classification Search ................... 604/20, 604/890.1
See application file for complete search history.

(56) References Cited

U.S. PATENT DOCUMENTS 6,398,562 B1 *    6/2002    Butler et al. .................. 439/91

FOREIGN PATENT DOCUMENTS

JP    11-076428    3/1999

* cited by examiner

*Primary Examiner*—Nicholas D Lucchesi
*Assistant Examiner*—Nathan R Price
(74) *Attorney, Agent, or Firm*—Pillsbury Winthrop Shaw Pittman LLP

(57) ABSTRACT

An apparatus for reverse iontophoresis has a base, an electrode provided on the base, an electrolytic gel provided on the electrode adapted for contacting a first part of a specimen, and for extracting a molecule from a first part of the specimen, a sensor chip placed underneath the electrolytic gel and having a pigment membrane containing a pigment that changes color by reaction with the molecule, a light source irradiating light on the pigment membrane, and a light sensor receiving a reflection of the light from the pigment membrane.

9 Claims, 5 Drawing Sheets

APPARATUS FOR REVERSE IONTOPHORESIS AND METHOD FOR REVERSE IONTOPHORESIS

CROSS REFERENCE TO RELATED APPLICATIONS

This application is based upon and claims the benefit of priority from prior Japanese Patent Application P2002-308574 filed on Oct. 23, 2002; the entire contents of which are incorporated by reference herein.

BACKGROUND OF THE INVENTION

1. Field of the Invention

The present invention relates to an apparatus for measuring a specific molecule included in a specimen and in particular to an apparatus and a method for reverse iontophoresis configured to extract the specific molecule electrically.

2. Description of the Related Art

Measuring blood sugar is a representative example for measuring a specific molecule concentration included in a specimen and especially in a living body. An existing method for measuring blood sugar is as follows. At first, blood is collected from vein with a syringe or by pricking part of the body with a needle and squeezing the body part to collect a blood sample. The collected blood is deposited on an optical sensor to react with pigments and enzymes as catalysts. Thereafter, by measuring absorbance of the reacted solvent, a concentration of the blood sugar included in the specimen is obtained as disclosed in Guilbault et al., "Advances in Biosensors" JAI Press, 1991, Vol. 1, pp 258-289. However, the existing method for measuring blood sugar using the syringe causes injury and pain.

On the other hand, an iontophoresis method recently became wide spread. An ionized molecule or a water-soluble molecule is introduced into the living body through the skin by iontophoresis as disclosed in published Japanese Patent Application H11-76428. In addition, a reverse iontophoresis method has also been studied recently. By the reverse iontophoresis method, the specific molecule is extracted from the living body through the skin with an electric current. Therefore, applying the reverse iontophoresis method to extract glucose from the living body without injury was attempted. However, the amount of extracted glucose by the reverse iontophoresis method is too small to analyze molecular concentration.

SUMMARY OF THE INVENTION

An aspect of present invention inheres in an apparatus for reverse iontophoresis configured such that it is contacted with a specimen having a base, an electrode provided on the base, an electrolytic gel provided on the electrode adapted for contacting a first part of the specimen, and for extracting a molecule from the first part of the specimen, a sensor chip placed underneath the electrolytic gel and having a pigment membrane containing a pigment that changes a color by reaction with the molecule, a light source irradiating light on the pigment membrane, and a light sensor receiving a reflection of the light from the pigment membrane.

Another aspect of the present invention inheres in a method for reverse iontophoresis including placing an electrolytic gel on an electrode connected to an anode of a power supply, contacting a first part of a specimen with the electrolytic gel and electrically connecting a second part of the specimen to a cathode of the power supply, applying a voltage between the first part and the second part by the power supply and extracting a molecule from the specimen to the electrolytic gel and transferring the molecule from the electrolytic gel to a pigment membrane, changing the color of the pigment membrane by reacting the molecule with the pigment membrane, irradiating a light on the pigment membrane and measuring a change in intensity of the light caused by the change in color of the pigment membrane.

DETAILED DESCRIPTION OF THE INVENTION

Figure 1:
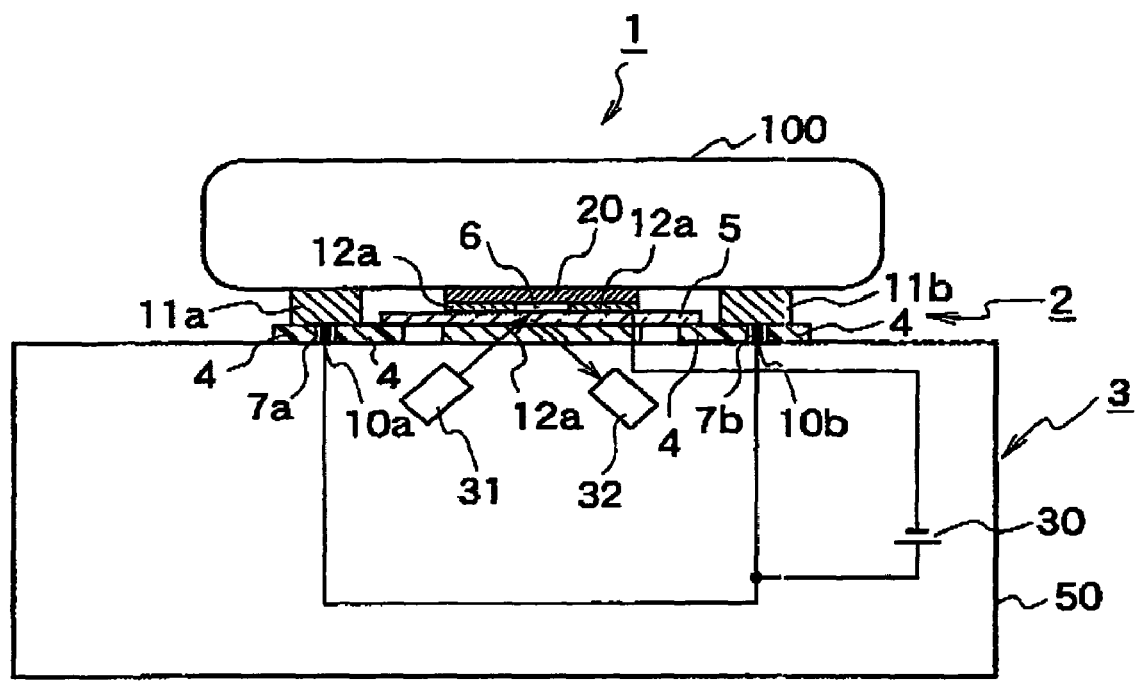
FIG. 1 is a sectional diagram of an apparatus for reverse iontophoresis in accordance with an embodiment of the present invention.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

With reference now to FIG. 1, an apparatus 1 for reverse iontophoresis in accordance with an embodiment of the present invention has a measuring device 3 and a sensor chip 2 placed on the measuring device 3.

Figure 2:
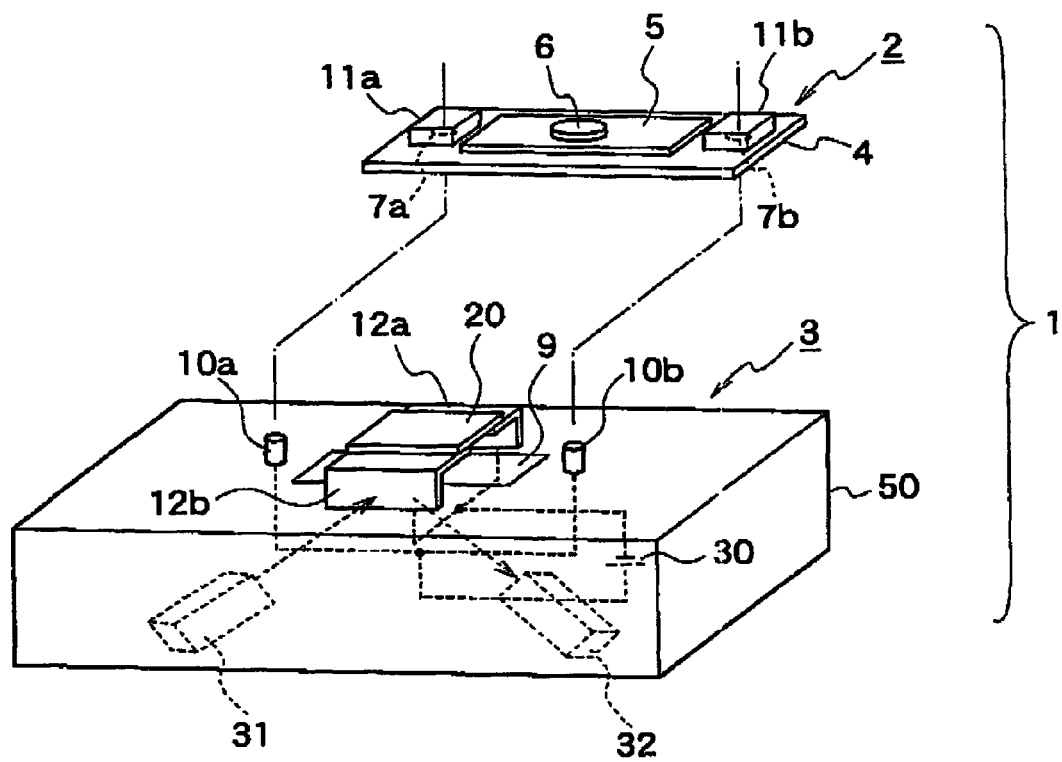
FIG. 2 is a diagram of an apparatus for reverse iontophoresis in accordance with an embodiment of the present invention.

With reference to FIG. 2, the sponsor chip 2 has a chip base 4, a glass chip 5 placed oil the chip base 4, and a pigment membrane 6 placed on the glass chip 5. The pigment membrane 6 contains allochroic pigments that react with a specific molecule extracted from a specimen. In addition, the sensor chip 2 has a first on-chip electrode 11a and a second on-chip electrode 11b respectively placed on both end of chip base 4. The glass chip 5 is made from borosilicate glass and the chip base 4 is made from plastics, for example. The pigment membrane 6 may contain a catalyst such as an enzyme to improve reactivity or a change of color. The first on-chip electrode 11a and the second on-chip electrode 11b are made from a conductive material such as aluminium (Al), gold (Au), silver (Ag), platinum (Pt) and stainless steel, for examples. Gel electrodes that provide good contact with the skin of the living body are also available for the first on-chip electrode 11a and the second on-chip electrode 11b. The first on-chip electrode 11a and the second on-chip electrode 11b are replaced after use.

Figure 3A:
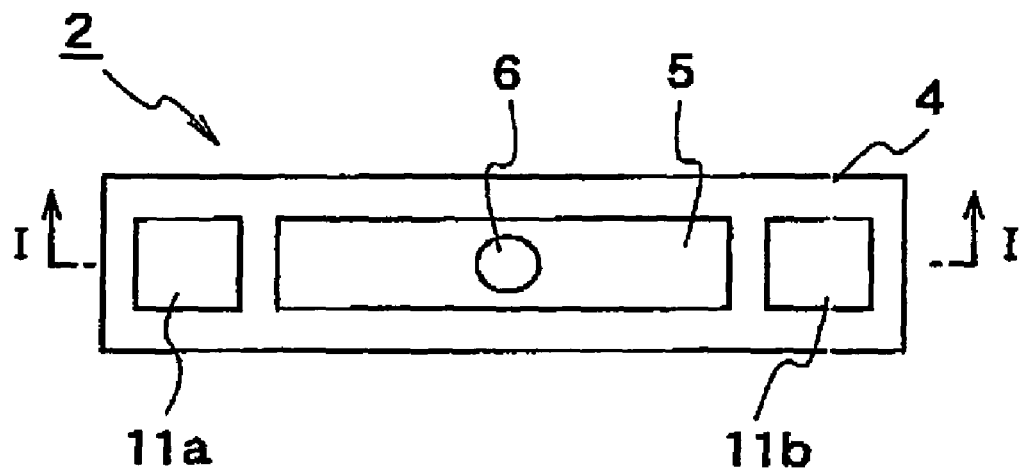
FIG. 3A is a plan view of a sensor chip in accordance with an embodiment of the present invention and FIG. 3B is a cross section of the sensor chip in a direction of a line I-I shown in FIG. 3A in accordance with an embodiment of the present invention.
Figure 3B:
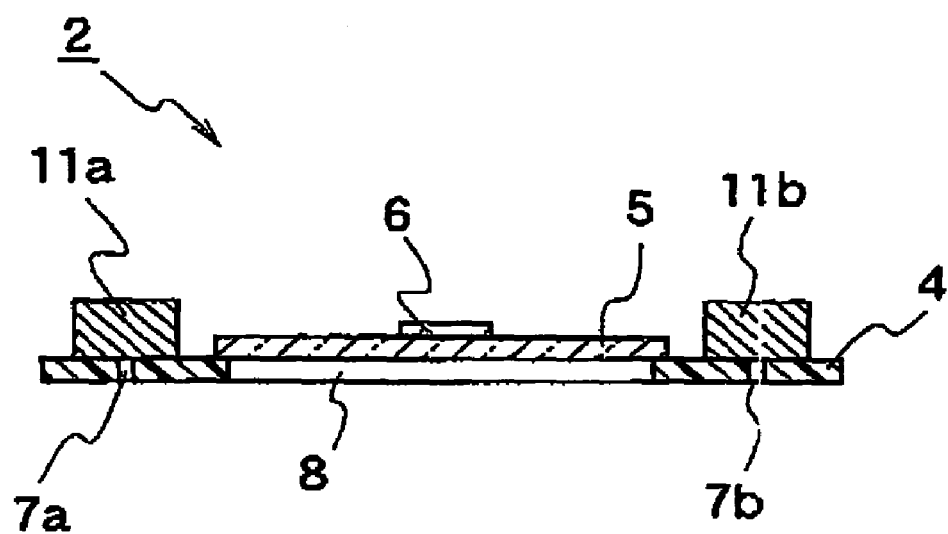

FIG. 3A shows a plan view of the sensor chip 2 and FIG. 3B shows a cross section of the sensor chip 2 In a direction of a line I-I shown in FIG. 3A. The chip base 4 has a first locating hole 7a and a second locating hole 7b in a vertical direction to principal plane as shown in FIG. 3B. The chip base 4 also has an observation opening 8 to allow laser beam directed to the pigment membrane 6 on the glass chip 5 to pass there through. The first on-chip electrode 11a and the second on-chip electrode 11b are placed over the first locating hole 7a and the second locating hole 7b of the chip base 4 respectively.

With reference again to FIG. 2, the measuring device 3 has a base 50, a first electrode 12a and a second electrode 12b placed on the base 50, an electrolytic gel 20 placed over the first electrode 12a and the second electrode 12b. In addition, the measuring device 3 has a light source 31 which irradiates a laser beam to the pigment membrane 6 on the sensor chip 2, a light sensor 32 receives the laser beam reflected from the pigment membrane 6 in the base 50. The base 50 has an observation opening 9 that allows the laser beam irradiated from the light source 31 to pass there through. The observation opening 9 is located at the center of the principal plane of the base 50. Further, a first conductive locating pin 10a and a second conductive locating pin 10b are provided on the principal plane of base 50. The first conductive locating pin 10a and the second conductive locating pin 10b is used to fix the sensor chip 2 with the first locating hole 7a and the second locating hole 7b. As is apparent, the first conductive locating pin 10a and the second conductive locating pin 10b are made from conductive material. In addition, the measuring device 3 has a power supply 30 in the base. An anode of the power supply 30 is connected to both the first electrode 12a and the second electrode 12b. A cathode of the power supply 30 is connected to both the first conductive loading pin 10a and the second conductive loading pin 10b. Both the first electrode 12a and the second electrode 12b can be separated from the base 50 to place the sensor chip 2 on the base 50 easily. In addition, the first electrode 12a and the second electrode 12b are movable in a vertical direction with respect to the principal plane of the base 50.

To set the sensor chip 2 on the measuring device 3, the sensor chip 2 is introduced into a space between the first electrode 12a and the second electrode 12b. Subsequently, the first conductive locating pin 10a and the second conductive locating pin 10b of the measuring device 3 are embedded in the sensor chip 2 through the first locating hole 7a and the second locating hole 7b. Consequently, the sensor chip 2 is correctly positioned on the base 50. In addition, the first conductive locating pin 10a and the second conductive locating pin 10b electrically contact with the first on-chip electrode 11a and the second on-chip electrode 11b respectively through the first locating hole 7a and the second locating hole 7b of the chip base 4. Therefore, the cathode of the power supply 30 is electrically connected to both the first on-chip electrode 11a and the second on-chip electrode 11b through the first conductive locating pin 10a and the second conductive locating pin 10b respectively as shown in FIG. 1.

A method for reverse iontophoresis in accordance with the embodiment of the present invention using the apparatus 1 for reverse iontophoresis is described below. As an example, a method for extracting glucose as a specific molecule from specimen 100 is represented.

(a) The sensor chip 2 is placed on the measuring device 3. The first conductive locating pin 10a and the second conductive locating pin 10b of the measuring device 3 are embedded in the sensor chip 2 through the first locating hole 7a and the second locating hole 7b. Consequently, the first conductive locating pin 10a and the second conductive locating pin 10b electrically contact with the first on-chip electrode 11a and the second on-chip electrode 11b respectively as shown in FIG. 1.

(b) The electrolytic gel 20 is placed on the first electrode 12a and the second electrode 12b straddling the pigment membrane 6 on the glass chip 5. Thereafter, the first conductive locating pin 10a and the second conductive locating pin 10b are electrically connected to the cathode of the power supply 30. The first electrode 12a and the second electrode 12b are electrically connected to the anode of the power supply 30. Consequently, the first on-chip electrode 11a and the second on-chip electrode 11b on the chip base 4 of the sensor chip 2 are electrically connected to the cathode of the power supply 30 through the first conductive locating pin 10a and the second conductive locating pin 10b. The power supply 30 generates, for example, a pulse electric field.

(c) One part of specimen 100 such as a skin part is pressed against the electrolytic gel 20 of the apparatus 1 for reverse iontophoresis. Further, another part of specimen 100 is pressed against the first on-chip electrode 11a and the second on-chip electrode 11b. Since the first electrode 12a and the second electrode 12b are movable in a vertical direction with respect to the principal plane of the base 50, the electrolytic gel 20 is held to the pigment membrane 6 on the sensor chip 2 as shown in FIG. 1. At this time, voltage of less than 20 volts is applied between the one part and another part of the specimen 100. Consequently, the glucose contained under the skin of the specimen is effectively extracted to the pigment membrane 6 through the electrolytic gel 20. The glucose reacts with the pigment contained in the pigment membrane 6 and changes the color of the pigment membrane 6. A range of the applied voltage is 5 volts to 20 volts or a narrower range to 10 volts to 15 volts. If the applied voltage is below 5 volt, resistance of the specimen 100, such as skin, affects a smooth flow of the electric current. Therefore, it takes an unacceptable long time to extract the glucose. In contrast, if the applied voltage is above 20 volt, damage to the specimen 100 may become a problem. For example, 0.3 mA/cm$^2$ of the electric current is selected to reduce damage to the specimen 100.

(d) The light source 31 such as a semiconductor laser oscillator and the light sensor 32 are placed symmetrically in the base 50 below the chip base 4 of the sensor chip 2 as shown in FIG. 1. For example, a 650 nm laser beam is irradiated on the under side of chip base 4 from the light source 31. The irradiated 650 nm laser beam reaches the pigment membrane 6 through the observation opening 8 and the transparent glass chip 5. At this time, the change in color of the pigment membrane 6 affects the absorbance of the pigment membrane 6. Consequently, intensity of the reflected laser beam changes. Therefore, the glucose concentration is measured by detecting transition of the reflected laser beam intensity with the light sensor 32.

As described above, the method for reverse iontophoresis using the apparatus for reverse iontophoresis in accordance with the embodiment of the present invention extracts a very small quantity of the specific molecule from the specimen 100 such as skin. In addition, the method and apparatus for reverse iontophoresis detect a modicum of the change in the reflected laser beam caused by the change in color of the pigment membrane 6 reacted with the extracted specific molecule. Therefore, the method and apparatus for reverse iontophoresis of the embodiment makes an accurate measurement of the extracted specific molecule concentration.

OTHER EMBODIMENTS

Although the invention has been described above by reference to the embodiment of the present invention, the present invention is not limited to the embodiment so described. Modifications and variations of the embodiment so described will occur to those skilled in the art, in the light of the above teachings.

Figure 4:
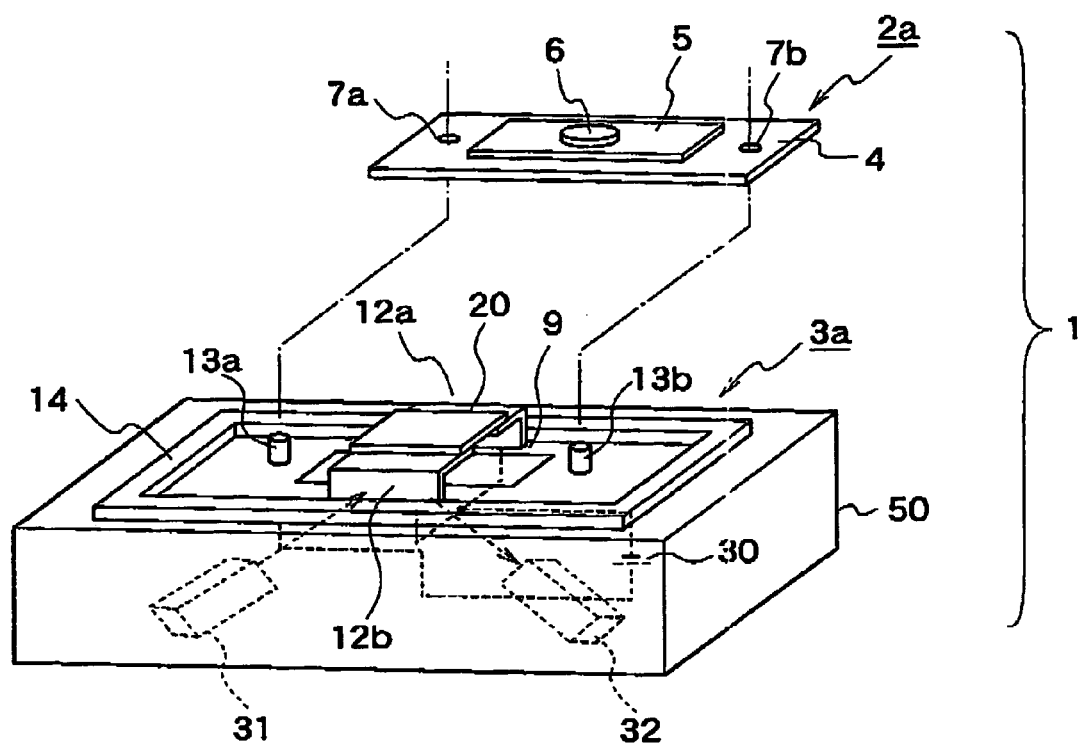
FIG. 4 is a diagram of an apparatus for reverse iontophoresis in accordance with other embodiment of the present invention.
Figure 5:
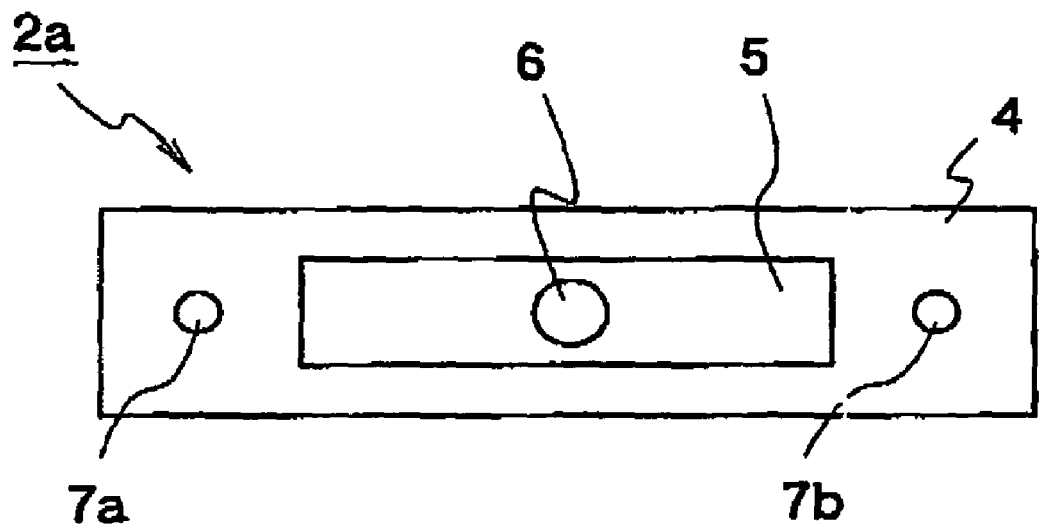
FIG. 5 and FIG. 6 are plan views of a sensor chip in accordance with other embodiment of the present invention.

For example, the first on-chip electrode 11a and the second on-chip electrode 11b placed on the chip base 4 of the sensor chip 2 are electrically connected to the power supply 30 through the first conductive locating pin 10a and the second conductive locating pin 10b as shown in FIG. 1. However, the present invention is not limited to the placement of the first on-chip electrode 11a and the second on-chip electrode 11b on the chip base 4 of the sensor chip 2. The apparatus 1 for reverse iontophoresis shown in FIG. 4 has a base electrode 14 on the base 50 as an alternative to the first on-chip electrode 11a and the second on-chip electrode 11b shown in FIG. 1. The base electrode 14 shown in FIG. 4 is placed on the principal plane of the base 50 and surrounds the sensor chip 4. In addition, a measuring device 3a has a first locating pin 13a and a second locating pin 13b on the principal plane of the base 50. The first locating pin 13a and the second locating pin 13b are embedded in the sensor chip 2a through the first locating hole 7a and the second locating hole 7b respectively. As shown in FIG. 5, the sensor chip 2a has the chip base 4, the glass chip 5 placed on the chip base 4, and the pigment membrane 6 placed on the glass chip 5. The chip base 4 has the first locating hole 7a and the second locating hole 7b. To set the sensor chip 2a on the measuring device 3a, the sensor chip 2 is introduced into a space between the first electrode 12a and the second electrode 12b. Thereafter, the first locating pin 7a and the second locating pin 7b of the measuring device 3a are embedded in the sensor chip 2a through the first locating hole 7a and the second locating hole 7b. Consequently, the sensor chip 2a is correctly positioned on the base 50. In addition, the cathode of the power supply 30 is electrically connected to the base electrode 14. The anode of the power supply 30 is electrically connected to the first electrode 12a and the second electrode 12b. The placement of other elements is similar to the apparatus 1 for reverse iontophoresis shown in FIG. 1.

Figure 6:
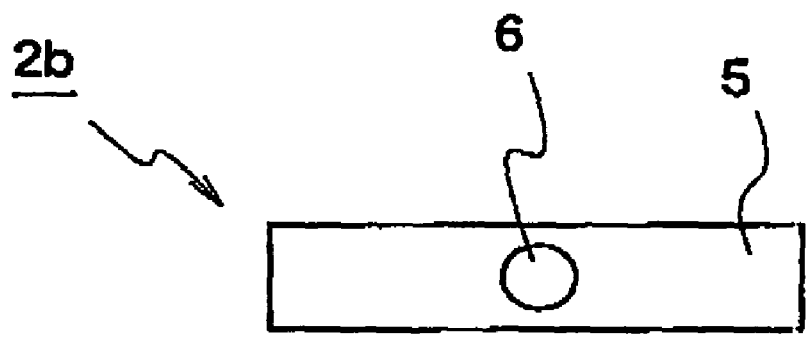

In addition, the glass chip 5 is placed on the chip base 4 in the case of both the sensor chip 2 shown in FIG. 3A and the sensor chip 2a shown in FIG. 5. This is because the glass chip 5 is obtained from a large glass plate divided by a scriber and the glass chip 5 is then milled. However, a sensor chip shown in FIG. 6 which does not have the chip base 4 also be used Further, the embodiment is explained in the context of extracting cationic molecules from the specimen 100. In contrast, the apparatus for reverse iontophoresis also extracts anionic molecules if the anode of power supply 30 is connected to the first conductive locating pin 10a and the second conductive locating pin 10b and the cathode of power supply 30 is connected to the first electrode 12a and the second electrode 12b.

As described above, the present invention includes many variations of embodiments. Therefore, the scope of the invention is defined with reference to the following claims.

What is claimed is:

1. An apparatus for reverse iontophoresis configured such that it is contacted with a specimen comprising:
    a base;
    a conductive locating pin provided on the base;
    an on-base electrode provided on the base;
    an electrolytic gel provided on the on-base electrode adapted for contacting a first part of the specimen, and for extracting a molecule from the first part of the specimen;
    a sensor chip disposed on the base and underneath the electrolytic gel, the sensor chip comprising a chip base having a locating hole, a pigment membrane disposed on the chip base and containing a pigment that changes color by reaction with the molecule, an on-chip electrode being disposed over the locating hole and adapted for electrically connecting to the conductive locating pin through the locating hole and for contacting a second part of the specimen;
    a light source irradiating light on the pigment membrane through an observation opening in the chip base; and
    a light sensor receiving a reflection of the light from the pigment membrane through the observation opening in the chip base.

2. The apparatus of claim 1, further comprising a power supply having an anode and a cathode electrically connected to the on-base electrode and the on-chip electrode, respectively.

3. The apparatus of claim 1, wherein the on-chip electrode is a gel electrode.

4. The apparatus of claim 1 further comprising a base electrode placed on the base for contacting a second part of the specimen.

5. The apparatus of claim 4 further comprising a power supply having an anode and a cathode electrically connected to the on-base electrode and the base electrode, respectively.

6. The apparatus of claim 4, wherein the base electrode is a gel electrode.

7. A method for reverse iontophoresis comprising:
    placing an electrolytic gel on an on-base electrode that is disposed on a base and is connected to an anode of a power supply;
    contacting a first part of a specimen with the electrolytic gel and electrically connecting a second part of the specimen to a cathode of the power supply through an on-chip electrode disposed on a chip base of a sensor chip disposed on the base and a conductive locating pin disposed on the base, the conductive locating pin passing through a locating hole of the chip base;
    applying a voltage between the first part and the second part by the power supply and extracting a molecule from the specimen to the electrolytic gel and transferring the molecule from the electrolytic gel to a pigment membrane;
    changing a color of the pigment membrane by reacting the molecule with the pigment membrane;
    irradiating a light on the pigment membrane; and
    measuring a change in intensity of the light caused by the change in the color of the pigment membrane.

8. The method of claim 7, wherein the voltage ranges from 5 volts to 20 volts.

9. The method of claim 7, wherein the voltage is a pulse voltage.

* * * * *